United States Patent [19]

Krutak et al.

[11] 4,447,624

[45] May 8, 1984

[54] PREPARATION OF THIOPHENES

[75] Inventors: James J. Krutak; Robert J. Maleski, both of Kingsport, Tenn.

[73] Assignee: Eastman Kodak Company, Rochester, N.Y.

[21] Appl. No.: 390,490

[22] Filed: Jun. 21, 1982

Related U.S. Application Data

[63] Continuation-in-part of Ser. No. 181,923, Aug. 27, 1980, abandoned.

[51] Int. Cl.$^3$ .................................................. C07D 333/36
[52] U.S. Cl. ..................................... 549/69; 544/146; 546/212; 546/213; 549/61; 549/64
[58] Field of Search ............................ 549/61, 64, 69; 546/212, 213; 544/146

[56] References Cited

PUBLICATIONS

Rajappa et al., Indian J. Chem., vol. 12 (1974), pp. 1–3; vol. 15B (1977), pp. 301–304; vol. 16B (1978), pp. 752–754.

Primary Examiner—Richard Raymond
Attorney, Agent, or Firm—Gary C. Bailey; Daniel B. Reece, III

[57] ABSTRACT

Process for the preparation of thiophenes having the structure

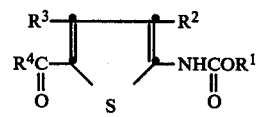

wherein $R^1$, $R^2$, $R^3$ and $R^4$ can be various substituents. The compounds can be converted to the corresponding 2-amino compounds from which azo dyes can be prepared.

5 Claims, No Drawings

PREPARATION OF THIOPHENES

This is a continuation-in-part application of Ser. No. 181,923, filed Aug. 27, 1980, now abandoned.

This invention pertains to the preparation of certain thiophene compounds which are useful in the preparation of azo dyes.

The proces of this invention provides for the preparation of a thiophene having the formula

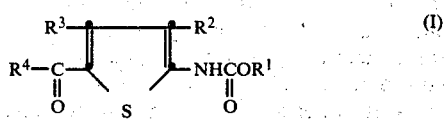

which comprises reacting an enamine having the formula

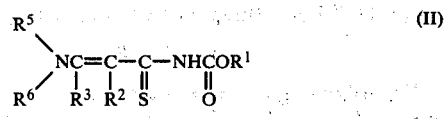

with a ketone having the formula

wherein

R¹ is an alkyl, cycloalkyl or aryl radical;

R² is hydrogen, an alkyl, cycloalkyl or aryl radical, or an acyl group (i.e. a residue of an acid), such as alkoxycarbonyl, carboxyl, cyano, carbamoyl, N-alkylcarbamoyl, N,N-dialkylcarbamoyl, N-arylcarbamoyl, alkanoyl, aroyl, piperidinocarbonyl, morpholinocarbonyl, sulfamoyl, N-alkylsulfamoyl, N,N-dialkylsulfamoyl, N-arylsulfamoyl, alkylsulfonyl, arylsulfonyl, piperidinosulfonyl, morpholinosulfonyl, alkylsulfinyl, arylsulfinyl, piperidinosulfinyl or morpholinosulfinyl;

R³ is hydrogen or an alkyl, cycloalkyl or aryl radical;

R⁴ is an alkyl, cycloalkyl, aryl or a heterocyclic aryl radical containing 5 or 6 ring members;

R⁵ and R⁶ are alkyl radicals or together R⁵ and R⁶ are tetramethylene, pentamethylene or 3-oxapentamethylene; and X is chloro or bromo.

The process can be carried out in an inert, organic solvent at a temperature in the range of about 15° to 200° C., preferably about 20° to 80° C., to give thiophenes (I) in good to excellent yields. Thiophenes (I) can be converted to the corresponding 2-aminothiophenes by using relatively mild conditions which, under certain conditions, do not affect other sensitive groups present on the thiophene compound.

Rajappa et al, Indian J. Chem., 12 (1974) 1–3, disclose that a good yield of thiophene (V) was obtained by the following reaction:

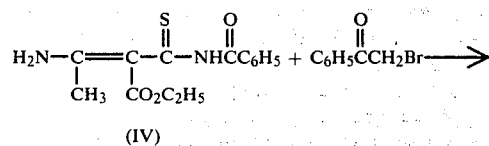

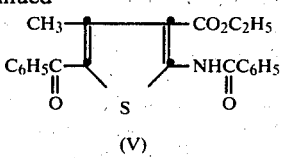

In our attempts to prepare thiophenes (I) using an enamine containing a primary amino group, i.e., enamine (II) wherein both R⁵ and R⁶ are hydrogen, the predominant product was a pyrimidine rather than the desired thiophene. We thus have discovered that in preparing thiophenes (I) containing the

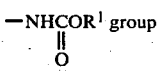

rather than a

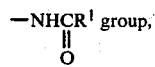

it is essential that the enamine contain a tertiary amine as is present in enamines (II).

The alkyl groups represented by R¹, R², R³ and R⁴ and the alkyl moieties of the other groups represented by R² can contain up to about 18 carbon atoms, preferably up to about 4 carbon atoms (referred to herein as "lower"). They can be substituted with various substituents which those skilled in the art will recognize as not affecting the course of the process, i.e., those that do not react with either (II) or (III). Examples of such substituents include hydroxy, lower alkoxy, cyano, nitro, succinimido, glutarimido, phthalimido, cyclohexyl, fluorenyl, aryl, fluorosulfonyl and groups having the formula —NH—Y—R⁷, —X—R⁷, —COO—R⁷, —OCOO—R⁷, —CONR⁸R⁹ and —SO₂NR⁸R⁹ wherein R⁸ is hydrogen, alkyl, cycloalkyl, or aryl and R⁹ is hydrogen or alkyl in which Y is —CO, —COO—, or —SO₂— and R⁷ is unsubstituted or substituted alkyl, cycloalkyl, or aryl or when Y is —CO—, R⁷ also can be amino, alkylamino, dialkylamino, arylamino, or furyl. The alkyl groups represented by R⁷ preferably are unsubstituted lower alkyl or lower alkyl substituted, for example, with halogen, aryl, cyano, lower alkylsulfonyl, hydroxy, lower alkylthio, lower alkanoyloxy, etc.

The carbocyclic aryl groups represented by R¹, R², R³ and R⁴ can contain up to about 18 carbon atoms and can be unsubstituted or substituted, for example, with alkyl or the substituents which can be present on the alkyl groups represented by R¹, R², R³ and R⁴. Examples of such aryl groups include unsubstituted and substituted phenyl and naphthyl.

The heterocyclic aryl groups which R⁴ can represent contain 5 or 6 ring members, are stabilized by resonance and can be unsubstituted or substituted with alkyl or with one or more of the substituents which can be present on the above-described alkyl radicals. Examples of the heterocyclic aryl groups include pyridyl, quinolyl, oxazolyl, benzoxazolyl, thiazolyl, benzothiazolyl, benzimidazolyl, oxadiazolyl, the thiadiazolyls, thienyl, pyrimidinyl, pyrazinyl, etc.

Of particular interest are compounds of formula (I) obtained from enamines wherein R² is an alkoxycarbonyl group having the formula —COO—R¹⁰ wherein $R^{10}$ is a carboxyl protecting group, i.e., a group which in conjunction with —COO— forms an ester from which a carboxyl group can be generated. The protecting group thus shields the carboxyl group from interfering reactions which can occur during later use of the thiophenes in the synthesis of azo dye intermediates. Examples of such groups are set forth in Chapter 5 of Halsam, Protective Groups in Organic Chemistry, Plenum Press (1973). Preferred of the groups represented by $R^{10}$ are lower alkyl such as 1,1-dimethylethyl; 2-cyanoethyl; 2,2,2-trichloroethyl; arylmethyl such as benzyl, p-methoxybenzyl, 2,4,6-trimethylbenzyl, and pentamethylbenzyl; benzhydryl; 2-arylsulfonylethyl such as 2-phenylsulfonylethyl; 2-aroylethyl such as 2-benzoylethyl; and phthalimidomethyl including substituted phthalimidomethyl such as 4-sulfamoyl- and 4-lower alkylsulfamoylphthalimidomethyl.

Examples of inert organic solvents which can be employed in the practice of our novel process include ethers such as diethyl ether, tetrahydrofuran and p-dioxane, alcohols such as methanol, isopropanol, and butanol, ether-alcohols such as 2-methoxyethanol and 2-(2-methoxyethoxy)ethanol, hydrocarbons such as hexane and toluene and pyridine compounds such as pyridine and the picolines.

The process of this invention is particularly suitable for the preparation of thiophenes (I) by reacting enamines (II) with a ketone having the formula

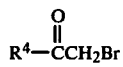

wherein:

$R^1$ is lower alkyl, 2,2,2-trichloroethyl, 1,1-dimethyl-2,2,2-trichloroethyl or phenyl;

$R^2$ is hydrogen, lower alkyl, phenyl, cyano, benzoyl or a group having the formula —COO—$R^{10}$ wherein $R^{10}$ is a carboxyl protecting group;

$R^3$ is hydrogen, lower alkyl or phenyl;

$R^4$ is lower alkyl, cyclohexyl or phenyl substituted with hydroxy, sulfamoyl, lower alkylsulfamoyl, sulfo, fluorosulfonyl, lower alkoxysulfonyl, carboxyl, lower alkylsulfonamido, arylsulfonamido, nitro, cyano, chloro, lower alkoxy or lower alkylsulfonyl; and $R^5$ and $R^6$ each is lower alkyl.

An especially preferred embodiment of our invention comprises the preparation of thiophenes of formula (I) which are unsubstituted in the four carbon position of the thiophene ring which are obtained from enamines wherein $R^3$ is hydrogen.

The process of this invention is further illustrated by the following examples.

EXAMPLE 1

A mixture of 25 g (0.061 m) of ethyl 2-[[(2,2,2-trichloroethoxycarbonyl)amino]thioxomethyl]-3-(diethylamino)-propenoate, 17.15 g (0.061 m) of m-fluorosulfonylphenacyl bromide, and 125 ml isopropyl alcohol was heated to reflux for five minutes. The reactants dissolved at reflux and shortly thereafter the product precipitated. The mixture was cooled and the solid collected by filtration. The solid was washed with isopropyl alcohol and then water to give 27.6 g (85%) of product, ethyl 5-[3-(fluorosulfonyl)benzoyl]-2-[[2,2,2-trichloroethoxycarbonyl]amino]-3-thiophene- carboxylate, melting point 108°-110° C. Ir 2.85, 5.72, 5.91, 6.09, 6.70, 7.10, 8.10, 8.42; NMR (CDCl₃) 10.7 (s,1); 8.40 (t,1); 8.2 (m,2); 7.8 (t,1); 7.70 (s,1); 4.90 (s,2); 4.37 (q,2); 1.36 (t,3). Anal: Calcd for $C_{17}H_{13}Cl_3FNO_7S_2$: C: 38.32; H: 2.46; N: 2.63; Found: C: 38.27; H: 2.60; N: 2.69.

This compound can be converted to the corresponding 2-amino compound by treating an isopropyl alcohol solution of it with zinc dust at reflux temperature.

EXAMPLE 2

A mixture of 130 g of ethyl 2-[[(phenoxycarbonyl)-amino]thioxomethyl]-3-(diethylamino)propenoate (0.37 mole), 104 g of m-fluorosulfonylphenacyl bromide (0.37 mole), and 350 ml of isopropanol was heated to reflux and held one hour. During this time, the reactants dissolved and the product precipitated. The mixture was cooled to 20°-25°, filtered, washed with isopropanol and then water to yield 133 g of white solid, ethyl 5-[3-(fluorosulfonyl)benzoyl]-2-[(phenoxycarbonyl)-amino]-3-thiophenecarboxylate, (75% yield), melting point 161°-163°. Ir: 2.88, 5.72, 5.98, 6.18, 7.12, 8.10, 8.40μ; NMR (CDCl₃) δ10.75 (s,1,N–H); 8.4 (m,1); 8.2 (m,2); 7.8 (m,1); 7.7 (s,1, thiophene-proton); 4.4 (q,2); 1.4 (t,3).

EXAMPLE 3

The following example illustrates the one-pot preparation of ethyl 5-[3-(fluorosulfonyl)benzoyl-2-[(ethoxycarbonyl)amino]-3-thiophene carboxylate starting with ethyl propiolate and diethylamine.

A solution of 1.96 g (0.02 mol) ethyl propiolate in 20 ml p-dioxane was stirred at 0°-5° C. and treated with 1.46 g diethylamine. The ice bath cooling was removed and an exothermic reaction occurred. The temperature increased to 35° C. but was checked there by ice bath cooling. After stirring 2 hours at 5°-25° C., 2.62 g (0.02 mol) ethoxycarbonyl isothiocyanate was added. After 3½ hours an additional 0.3 g ethoxycarbonyl isothiocyanate (3) was added. One and one-half hours later a solution of 5.62 g (0.02 mol) m-fluorosulfonylphenacyl bromide in 15 ml p-dioxane was added at 8°. An exothermic reaction occurred. The temperature increased unchecked to 33° C. The reaction was stirred for several hours and filtered. The solid product collected was washed with isopropanol and then water and air dried to give 4.12 g thiophene product, m.p. 131-132. From the filtrate was obtained 2.89 g additional product. Total yield 7.01 g (82%). The structure was assigned on the basis of infrared, NMR, and elemental analysis. Anal. Calcd. for $C_{17}H_{16}FNO_7S_2$: C, 47.55; H, 3.76; N, 3.26. Found: C, 47.55; H, 3.85; N, 3.20.

EXAMPLE 4

A mixture of 15 g (0.41 mole) 1,1-dimethylethyl-3-(diethyl)amino-2-[[(phenoxycarbonyl)amino]thioxomethyl]-2-butenoate and 8.19 g (0.041 mole) phenacyl bromide in 100 ml isopropyl alcohol was refluxed for one hour and stirred one hour at room temperature. The solid product was filtered and washed in succession with isopropanol, water, and isopropanol. After air drying, the product, 1,1-dimethylethyl-5-benzoyl-4-methyl-2-[(phenoxycarbonyl)amino]-3-thiophenecarboxylate, weighed 16.5 g (92%) and had a melting point of 183° C. The structure was established by infrared, NMR, and elemental analyses. Anal. Calcd. for $C_{24}H_{23}NO_5S$: C, 65.88; H, 5.30; N, 3.20 Found: C, 65.72; H, 5.33; N, 3.32.

If Example 2 is repeated using 1,1-dimethylethyl 3-amino-2-[[(phenoxycarbonyl)amino]thioxomethyl]-2-butenoate as the enamine reactant and phenacyl bromide as the ketone reactant, the predominant product obtained is 1,1-dimethylethyl 4-[(benzoylmethyl)thio]-1,2-dihydro-6-methyl-2-oxo-5-pyrimidinecarboxylate having the structure

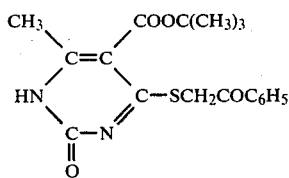

The compounds set forth in the following examples further illustrate the thiophenes of formula (I) which can be prepared according to the process of this invention.

| Example | R¹ | R² | R³ | R⁴ | Melting Point, °C. |
|---|---|---|---|---|---|
| 5 | —C₂H₅ | —COCH₃ (C=O) | H | ⟨phenyl-CH₃, SO₂F⟩ | 153–155 |
| 6 | —C₂H₅ | —COC₂H₅ (C=O) | H | —CH₃ | 95–96.5 |
| 7 | —CH₂CCl₃ | —COC₂H₅ (C=O) | H | C₆H₅ | 123–125 |
| 8 | —CH₂CCl₃ | —COC₂H₅ (C=O) | H | ⟨phenyl-CH₃, SO₂F⟩ | 108–110 |
| 9 | —CH₂CH₂Cl | —COC₂H₅ (C=O) | H | ⟨phenyl-CH₃, SO₂F⟩ | 136–137 |
| 10 | —C₆H₅ | —COC₂H₅ (C=O) | H | —CCH₃ (C=O) | 131–133 |
| 11 | —C₆H₅ | —COC₂H₅ (C=O) | H | ⟨phenyl-CH₃, SO₂F⟩ | 160–162 |
| 12 | —C₆H₅ | —CN | H | —C₆H₅ | 204–211 |
| 13 | —C₂H₅ | —CN | H | —C₆H₅ | 164–166 |
| 14 | —C₂H₅ | —CC₆H₅ (C=O) | H | —C₆H₅ | 148–150.5 |
| 15 | —C₂H₅ | —CC₆H₅ (C=O) | H | ⟨phenyl-CH₃, SO₂F⟩ | 197–198.5 |

-continued

| Example | R¹ | R² | R³ | R⁴ | Melting Point, °C |
|---|---|---|---|---|---|
| 16 | −CH₂−(fluorenyl) | −COC₂H₅ (with =O) | H | phenyl−SO₂F | 158−160 |
| 17 | −C₆H₅ | −COC₂H₅ (with =O) | H | phenyl−Br | 172−174 |
| 18 | −C₆H₅ | −COC₂H₅ (with =O) | H | thienyl (S) | 163−164.5 |
| 19 | −C₆H₅ | −COC₂H₅ (with =O) | H | thienyl with −COC₂H₅ and −NHCOCH₂CCl₃ | 180−181 |
| 20 | −CH₂CCl₃ | −COC₂H₅ (with =O) | H | phenyl−OCCH₃ (with =O) | 142−143.5 |
| 21 | −C₆H₅ | −COC₂H₅ (with =O) | H | phenyl−NO₂ | 140.5−141.5 |
| 22 | −C₂H₅ | −COC₂H₅ (with =O) | H | phenyl−SO₂−N(pyrazolyl) | 159−161 |
| 23 | −C₆H₅ | −COC₂H₅ (with =O) | H | thienyl with −COC₂H₅ and −NHCOC₆H₅ | 221−222 |
| 24 | −C(CH₃)₂−CCl₃ | −COC₂H₅ (with =O) | H | thienyl with −COC₂H₅ and −NHCOC(CH₃)₂CCl₃ | 263−264 |
| 25 | −C₆H₅ | −COC₂H₅ (with =O) | H | naphthyl | 121−123 |

-continued

| Example | R¹ | R² | R³ | R⁴ | Melting Point, °C. |
|---|---|---|---|---|---|
| 26 | —CH₂CCl₃ | —COC(CH₃)₃ | | phenyl with —OCCH₃ (O) | 155–156 |
| 27 | —CH₂CCl₃ | —COCH₂CH₂CN | | phenyl with —OCCH₃ (O) | 136–137 |
| 28 | —C₆H₅ | —COC₂H₅ | | —CH₂Br | 111–113 |
| 29 | —CH₂CCl₃ | —COCH₂CH₂CN | | phenyl with —OCOCH₂Cl₃ | 146–148 |
| 30 | —C₆H₅ | —COCH₂CH₂CN | H | thiophene with —CCH₂CH₂CN (O) and —NHCOC₆H₅ | 220–222 |
| 31 | —CH₂CCl₃ | —COCH₂CF₃ | H | phenyl with —SO₂F | 131.5–133.5 |
| 32 | —CH₂CCl₃ | —COCH₂CH₂CN | H | phenyl with —SO₂NH₂ | 177–178 |
| 33 | —CH₂CCl₃ | —COCH₂CH₂CN | H | naphthyl with —OCC₆H₅ (O), —CON(C₁₈H₃₇)₂, —NHO₂S-phenyl | — |
| 34 | —CH₂CCl₃ | —COCH₂CH₂CN | H | phenyl with —OH | 176–178 |
| 35 | —CH₂CCl₃ | —COCH₂N(phthalimide) | H | —C₆H₅ | 188–190 |

| Example | R[1] | R[2] | R[3] | R[4] | Melting Point, °C. |
|---|---|---|---|---|---|
| 36 | —CH$_2$CCl$_3$ | —COCH$_2$N(phthalimido) | H | OH (hydroxyphenyl) | 174–176 |

The invention has been described in detail with particular reference to certain preferred embodiments thereof, but it will be understood that variations and modifications can be effected within the spirit and scope of the invention.

We claim:

1. A process for the preparation of a thiophene having the formula $$\begin{array}{c} R^3 \diagup\!\!\!\!\diagdown R^2 \\ R^4-\underset{\underset{O}{\|}}{C}\diagdown_S\diagup \text{NHCOR}^1 \\ \phantom{xxxxxxxx}\overset{\|}{O} \end{array}$$

which comprises reacting an enamine having the formula $$\underset{R^6}{\overset{R^5}{\diagdown}}N-C=\underset{\underset{R^2}{|}}{\underset{R^3}{|}}C-\underset{\underset{O}{\|}}{\overset{\|}{C}}-\text{NHCOR}^1 \\ \phantom{xxxxxxx} S$$

with a ketone having the formula $$R^4-\overset{O}{\overset{\|}{C}}CH_2-X$$

wherein

R$^1$ is an alkyl, cycloalkyl or aryl;

R$^2$ is hydrogen, an alkyl, cycloalkyl or aryl radical, alkoxycarbonyl, substituted alkoxycarbonyl, carboxyl, cyano, carbamoyl, N-alkylcarbamoyl, N,N-dialkylcarbamoyl, N-carbocyclic arylcarbamoyl, alkanoyl, carbocyclic aroyl, piperidinocarbonyl, morpholinocarbonyl, sulfamoyl, N-alkylsulfamoyl, N,N-dialkylsulfamoyl, N-carbocyclic arylsulfamoyl, alkylsulfonyl, carbocyclic arylsulfonyl, piperidinosulfonyl, morpholinosulfonyl, alkylsulfinyl, carbocyclic arylsulfinyl, piperidinosulfinyl or morpholinosulfinyl radical;

R$^3$ is hydrogen or an alkyl, cycloalkyl or carbocyclic aryl radical;

R$^4$ is an alkyl, cycloalkyl or carbocyclic aryl radical;

R$^5$ and R$^6$ are alkyl radicals or together R$^5$ and R$^6$ are tetramethylene, pentamethylene or 3-oxapentamethylene; and X is chloro or bromo.

2. A process according to claim 1 wherein R$^2$ has the formula —COO—R$^{10}$ wherein R$^{10}$ is a carboxyl protecting group.

3. A process according to claim 1 wherein R$^2$ has the formula —COOR—R$^{10}$ wherein R$^{10}$ is lower alkyl, 2-cyanoethyl, carbocyclic arylmethyl, benzhydryl, 2-carbocyclic arylsulfonylethyl, 2-carbocyclic aroylmethyl, phthalimidomethyl and phthalimidomethyl substituted at the 4-position with sulfamoyl or lower alkylsulfamoyl.

4. A process for the preparation of a thiophene having the formula $$\begin{array}{c} R^3 \diagup\!\!\!\!\diagdown R^2 \\ R^4-\underset{\underset{O}{\|}}{C}\diagdown_S\diagup \text{NHCOR}^1 \\ \phantom{xxxxxxxx}\overset{\|}{O} \end{array}$$

which comprises reacting an enamine having the formula $$\underset{R^6}{\overset{R^5}{\diagdown}}N-C=\underset{\underset{R^2}{|}}{\underset{R^3}{|}}C-\underset{\underset{O}{\|}}{\overset{\|}{C}}-\text{NHCOR}^1 \\ \phantom{xxxxxxx} S$$

with a ketone having the formula $$R^4-\overset{O}{\overset{\|}{C}}CH_2-Br$$

wherein

R$^1$ is lower alkyl, 2,2,2-trichloroethyl, 1,1-dimethyl-2,2,2-trichloroethyl or phenyl;

R$^2$ is hydrogen, lower alkyl, phenyl, cyano, benzoyl or a group having the formula —COO—R$^{10}$ wherein R$^{10}$ is a carboxyl protecting group;

R$^3$ is hydrogen, lower alkyl or phenyl;

R$^4$ is lower aklkyl, cyclohexyl or phenyl substituted with hydroxy, sulfamoyl, lower alkylsulfamoyl, sulfo, fluorosulfonyl, lower alkoxysulfonyl, carboxyl, lower alkylsulfonamido, carbocyclic arylsulfonamido, nitro, cyano, chloro, lower alkoxy or lower alkylsulfonyl; and R$^5$ and R$^6$ each is lower alkyl.

5. A process for the preparation of a thiophene having the formula $$\begin{array}{c} R^3 \diagup\!\!\!\!\diagdown R^2 \\ R^4-\underset{\underset{O}{\|}}{C}\diagdown_S\diagup \text{NHCOR}^1 \\ \phantom{xxxxxxxx}\overset{\|}{O} \end{array}$$

which comprises reacting an enamine having the formula

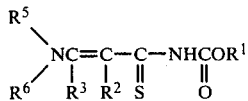

with a ketone having the formula

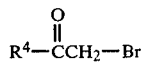

wherein $R^1$ is lower alkyl, 2,2,2-trichloroethyl, 1,1-dimethyl-2,2,2-trichloroethyl or phenyl;

$R^2$ is hydrogen, lower alkyl, phenyl, cyano, benzoyl or a group having the formula —COO—$R^{10}$ wherein $R^{10}$ is a carboxyl protecting group;

$R^3$ is hydrogen;

$R^4$ is lower alkyl, cyclohexyl or phenyl substituted with hydroxy, sulfamoyl, lower alkylsulfamoyl, sulfo, fluorosulfonyl, lower alkoxysulfonyl, carboxyl, lower alkylsulfonamido, carbocyclic arylsulfonamido, nitro, cyano, chloro, lower alkoxy or lower alkylsulfonyl; and $R^5$ and $R^6$ each is lower alkyl.

* * * * *

UNITED STATES PATENT AND TRADEMARK OFFICE
CERTIFICATE OF CORRECTION

PATENT NO. : 4,447,624
DATED : May 8, 1984
INVENTOR(S) : James J. Krutak and Robert J. Maleski It is certified that error appears in the above-identified patent and that said Letters Patent is hereby corrected as shown below:

Column 11, line 66, "-COOR-$R^{10}$" should read --- -COO-$R^{10}$ ---.

Column 12, line 52, "aklkyl," should read --- alkyl, ---.

Signed and Sealed this

Eighteenth Day of December 1984

[SEAL]

Attest:

GERALD J. MOSSINGHOFF

*Attesting Officer*  *Commissioner of Patents and Trademarks*